United States Patent [19]

McAlpine

[11] 4,226,979
[45] Oct. 7, 1980

[54] FORTIMICIN AK

[75] Inventor: James B. McAlpine, Libertyville, Ill.

[73] Assignee: Abbott Laboratories, North Chicago, Ill.

[21] Appl. No.: 25,241

[22] Filed: Mar. 29, 1979

[51] Int. Cl.$^2$ .................. A61K 31/71; C07H 15/22
[52] U.S. Cl. .................. 536/17 R; 424/180; 536/18
[58] Field of Search ........................................ 536/17

[56] References Cited

U.S. PATENT DOCUMENTS 4,091,032  5/1978  Tadanier et al. .................. 536/17
4,124,756  11/1978  Martin et al. .................. 536/17

Primary Examiner—Johnnie R. Brown
Attorney, Agent, or Firm—Gildo E. Fato; Robert L. Niblack; Joyce R. Niblack

[57] ABSTRACT

A new fortimicin, fortimicin AK. The compound is coproduced in the fermentation of *Micromonospora olivoasterospora* ATCC No. 21819, 31009 or 31010 along with fortimicin A, fortimicin B isofortimicin, fortimicin E and a number of other minor factors. The compound is useful as an intermediate in synthesizing fortimicin AK derivatives which are useful as antibiotics.

1 Claim, No Drawings

FORTIMICIN AK

BACKGROUND OF THE INVENTION

The aminoglycoside antibiotics are a valuable therapeutic class of antibiotics which include the kanamycins, gentamicins, streptomycins, sagamicins and the more recently discovered fortimicins. While the naturally produced parent antibiotics are generally, in themselves, valuable antibiotics, chemical modifications have been found to improve the activity, either intrinsic activity or activity against resistant strains or against one or more strains the parent antibiotic is not effective against. Thus, chemical modification has provided both alternative therapeutic agents as well as those which are held in reserve because of the resistance problem. And, because of the development of aminoglycoside-resistant strains and inactivation of the parent antibiotics by R-mediated factors which can develop, the search for new therapeutic entities continues.

Further, some of the naturally produced, parent antibiotics, such as fortimicin B and fortimicin E, are primarily useful as intermediates in preparing derivatives which have more potent antibacterial properties than their weakly active parent antibiotics. The present invention provides one such fortimicin, fortimicin AK.

The fortimicin of this invention is co-produced in the fermentation of *Micromonospora olivoasterospora* ATCC No. 21819, 31009 or 31010 according to the method of Nara et al. U.S. Pat. Nos. 3,931,400 and 3,976,768 which disclose the production of fortimicin A and fortimicin B.

Fortimicin AK is a minor factor which is co-produced with fortimicin A, fortimicin B and a number of other minor factors which are the subject of copending, commonly assigned patent application Ser. Nos. 025,243; 025,247; 025,250; 025,251 and 025,252 filed of even date herewith and with the minor factors disclosed and claimed in commonly assigned, copending United States patent application Ser. Nos. 863,016 and 863,015, both filed Dec. 21, 1977.

SUMMARY OF THE INVENTION

The present invention provides a new fortimicin, fortimicin AK. The fortimicin of this invention is useful as an intermediate in preparing fortimicin derivatives which are useful as antibiotics against susceptible gram positive and gram negative bacilli such as *Escherichia coli, Staphylococcus aureus, Pseudomonas aeruginosa, Bacillis subtilis, Proteus vulgaris, Shigella sonnei, Salmonella typhi* and *Klebsiella pneumonia.*

DETAILED DESCRIPTION OF PREFERRED EMBODIMENTS

The compound of this invention, fortimicin AK is represented by the Formula:

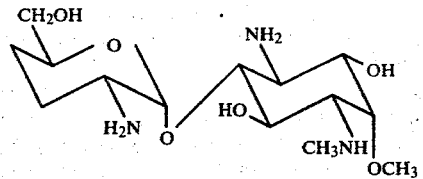

Fortimicin AK is useful as an intermediate in the preparation of fortimicin derivatives such as the 4-N-acyl, 2'-N-acyl, 4,2'-N,N-diacyl, 4-N-alkyl, 2'-N-alkyl, 4,2'-di-N-alkyl and like derivatives which are disclosed and claimed in commonly assigned, copending application Ser. No. 025,242, filed of even date herewith.

Illustrative of fortimicin AK derivatives which can be prepared from the compound of this invention are derivatives represented by Formula II:

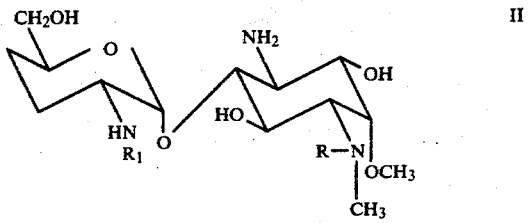

wherein: R and $R_1$ are the same or different members of the group consisting of hydrogen, acyl, aminoacyl, diaminoacyl, N-loweralkylaminoacyl, N,N-diloweralkylaminoacyl, hydroxy-substituted aminoacyl, loweralkyl, aminoloweralkyl, diaminoloweralkyl, hydroxyloweralkyl, N-loweralkylaminoloweralkyl, aminohydroxyloweralkyl, N,N-diloweralkylaminoloweralkyl, N-loweralkylaminohydroxyloweralkyl, N,N-diloweralkylaminohydroxyloweralkyl and the pharmaceutically acceptable salts thereof.

The term "acyl", as used in the above definitions refers to acyl radicals of loweralkylcarboxylic acids represented by the formula

wherein R is loweralkyl, i.e., acetyl, propionyl, butyryl, valeryl, etc.

The terms aminoacyl, hydroxy-substituted aminoacyl, etc., enumerated in the definitions of R and $R_1$ for formula II include, but are not limited to as will be obvious to those skilled in the art, naturally occuring amino acids such as glycyl, valyl, alanyl, sarcosyl, leucyl, isoleucyl, prolyl, seryl, and like amino acid residues as well as groups such as 2-hydroxy-4-aminobutyryl and like groups. The amino acid residues included in the above terms, with the exception of glycyl, can be either in the L- or D-configurations or mixtures thereof.

The term "loweralkyl", as used herein, refers to straight or branched chain alkyl radicals containing from 1 to 6 carbon atoms and includes, but is not limited to, methyl, ethyl, n-propyl, iso-propyl, n-butyl, iso-butyl, tert-butyl, n-pentyl, 1-methylbutyl, 2,2-dimethylpropyl, n-hexyl, 2-methylpentyl and the like radicals.

The term "pharmaceutically acceptable salts refers to the non-toxic acid addition salts of the compounds of Formulae I and II which can be prepared either in situ during the final isolation and purification or by separately reacting the free base with a suitable organic or inorganic acid by methods well known in the art. Representative salts include the mono-, di-, tri- or other per-salts such as the hydrochloride, hydrobromide, sulfate, bisulfate, acetate, oxalate, valerate, oleate, palmitate, stearate, laurate, borate, benzoate, lactate, phosphate, tosylate, citrate, maleate, fumarate, succinate, tartrate, napsylate and like salts.

The antibiotics of Formula II are effective antibacterial agents against susceptible or sensitive strains of gram-negative and gram-positive bacilli such as *Staphy-* lococcus aureus, Escherichia coli, Pseudomonas aeruginosa, Bacillus subtilis, Proteus vulgaris, Shigella sonnei, Salmonella typhi and Klebsiella pneumoniae. The compounds of Formula II are administered parenterally, i.e., intravenously, intramuscularly, intraperitoneally or subcutaneously for systemic effect in daily dosages of from 20 to 40 mg/kg of body weight daily, preferrably from 25 to 30 mg/kg of body weight daily based on lean body weight as is good medical practice with the aminoglycoside antibiotics and are preferrably administered in divided dosages. The compounds can also be administered orally at the above dosages to sterilize the intestinal tract and can further be administered in suppository form.

The term "sensitive or susceptible strains" refers to strains of bacilli or organisms which have been demonstrated to be sensitive to a particular antibiotic in a standard in vitro sensitivity test and thus in vitro activity has been established for a particular antibiotic against a specific strain of a specific organism.

Fortimicin AK can be prepared by the fermentation of *Micromonospora olivoasterospora* ATCC No. 21819, 31009 or 31010 according to the methods described by Nara et al. in U.S. Pat. Nos. 3,931,400 and 3,976,768 for the fermentation of fortimicin A and fortimicin B, and set forth in Examples 1–4 for the fermentation and isolation of fortimicin AK.

The 4-N-acyl fortimicin AK derivatives are prepared following the general procedure used for the preparation of 4-N-acyl derivatives of fortimicins having the fortimicin E stereochemistry for the 4-N-position as disclosed in commonly assigned, co-pending U.S. application Ser. No. 863,010, filed Dec. 21, 1977.

Generally speaking, the 4-N-acyl derivatives can be prepared by reacting 2-moles of salicylaldehyde with fortimicin AK which results in the formation of 1,2'-di-N-salicylaldehyde Schiff base fortimicin AK. The latter can then be aminoacylated by coupling the Schiff base intermediate with a variety of activated carboxylic acid derivatives such as a carboxylic acid anhydride, a carboxylic acid chloride, an active carboxylic acid ester or a carboxylic acid azide.

The active esters may be conveniently prepared by reacting the appropriate carboxylic acid, $R_1COOH$ with, for example 1-hydroxybenzotriazole, N-hydroxysuccinimide or N-hydroxy-5-norbornene-2,3-dicarboximide according to the method of M. Fujino et al., *Chem. Pharm Bull,* Japan 22: 1857 (1974) wherein $R_1$ is as defined in formula II for acyl and acyl-containing groups.

For example, the Schiff base fortimicin AK can be aminoacylated with an active ester represented by the formula $A-R_1Z$, i.e., N-benzyloxycarbonylglycyl-N-hydroxysuccinimide active ester (A=ONS, R=COCH$_2$NH—), N-benzyloxycarbonyl-β-alanyl-N-hydroxy-5-norbornene-2,3-dicarboximide active ester (A=ONB, R=COCH$_2$CH$_2$NH—), N-benzyloxycarbonylsarcosyl-N-hydroxy-5-norbornene-2,3-dicarboximide active ester (A=ONB), R=COCH$_2$N(CH$_3$)—), and N-benzyloxycarbonyl-L-(2-hydroxy-4-amino)butyryl-N-hydroxy-5-norbornene-2,3-dicarboximide active ester (A=ONB, R=COCH(OH)CH$_2$CH$_2$NH—) where the symbol Z referes to the benzyloxycarbonyl group

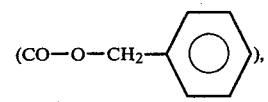

ONB refers to N-hydroxynorbornyldicarboximide and ONS refers to N-(benzyloxycarbonyloxy)succinimide.

After the above illustrative couplings, the following intermediates are obtained: 4-N-(N-benzyloxycarbonylglycyl)-1,2'-di-N-salicylaldehyde Schiff base fortimicin AK; 4-N-(N-benzyloxycarbonyl)-β-alanyl)-1,2'-di-N-salicylaldehyde Schiff base fortimicin AK; 4-N-(N-benzyloxycarbonylsarcosyl)-1,2'-N-salicylaldehyde Schiff base fortimicin AK; and 4-N-[N-benzyloxycarbonyl-(L-2-hydroxy-4-aminobutyryl)]-1,2'-di-N-salicylaldehyde Schiff base fortimicin AK respectively.

It will be readily apparent to those skilled in the art that by substituting the appropriate R group, any of the acyl-containing R intermediates for the corresponding final products can be obtained.

The Schiff base intermediates are treated with 0.2 N aqueous hydrochloric acid to cleave the Schiff base protecting groups and the resulting crude dihydrochloride salts are subjected to silica gel chromatography in a solvent system containing ammonium hydroxide which results in the following illustrative, partially deprotected intermediates: 4-N-(N-benzyloxycarbonylglycyl)fortimicin AK; 4-N-(N-benzyloxycarbonyl-β-alanyl)fortimicin AK; 4-N-(N-benzyloxycarbonylsarcosyl)fortimicin AK; and 4-N-[N-benzyloxycarbonyl-(L-2-hydroxy-4-aminobutyryl)]fortimicin AK. The 4-N-protected intermediates are then reacted with N-benzyloxycarbonyloxy-5-norbornene-2,3-dicarboximide(A-ONB) to form the corresponding tri-N-protected intermediates, i,e, tri-N-benzyloxycarbonyl-4-N-glycylfortimicin AK.

Hydrogenolysis of the tri-N-protected intermediate over palladium on carbon catalyst (5% Pd/C) in, for example 0.2 N hydrochloric acid in methanol yields the desired final products, i.e. 4-N-glycylfortimicin AK trihydrochloride, 4-N-sarcosylfortimicin AK trihydrochloride, etc.

4-N-alkylation is readily accomplished by reducing the corresponding acyl, hydroxyacyl or amino-containing acyl product with diborane.

2'-N-acylation is accomplished by rearrangement of the corresponding 4-N-derivative bearing the desired R substituent, prepared as above described, by for example, converting the stable acid addition salts to the free bases with the use of a suitable anion exchange resin and placing the desired 4-N-substituted free base in water which readily rearranges the C$_4$-nitrogen substituent to the nitrogen atom attached to the C$_2$'-carbon. Treatment of the 2'-N-substituted fortimicin with a suitable N-acylating agent such as N-(benzyloxycarbonyloxy)succinimide, etc., as described above, in a solvent system such as N,N-dimethylformamide-methanol-water, results in 1-N-protection and the 1-N-protected intermediate can then be N-acylated at the 4-position as described above to provide the 4,2'-di-N-acyl derivatives of the fortimicin of this invention, using the term acyl broadly to encompass the "acyl"-containing definitions for R and $R_1$ of Formula II.

2'-N-alkylation is achieved, as described above, by reducing the appropriate C$_2$'-N-acyl substituent with a suitable reducing agent such as diborane or a metal hydride such as lithium aluminum hydride. The resulting 2'-N-alkyl derivatives can then be 4-N-acylated as described above to provide 2'-N-alkyl-4-N-acyl derivatives.

The 4,2'-di-N-alkyl derivatives can be prepared by treating the appropriate 4,2'-di-N-acyl derivatives, suitable N-protected, with a suitable reducing agent as described above and deblocking by hydrogenolysis.

It is to be understood that the terms acyl and alkyl have, for the purpose of the above discussion have been used as shorthand references to the terms "loweralkyl" and "acyl" defined on pages 3 and 4 of the specification and to the acyl and alkyl-containing definitions for R and $R_1$ is Formula II. This shorthand reference has been used to simplify the above discussion, not to modify the terms as defined.

The following Examples further illustrate the present invention by setting forth the fermentation and isolation of fortimicin AK which is coproduced with fortimicin A, fortimicin B, isofortimicin, fortimicin E and a number of other minor factors.

Fortimicin AK can be prepared by the fermentation of *Micromonospora olivoasterospora* ATCC 21819 in a suitable fermentation broth and isolated as described hereinbelow.

EXAMPLE 1

Preparation of Fermentation Broth

6000 Liters of a fermentation broth having the following composition and pH 7 before sterilization is prepared:

| Ingredient | Weight Percent |
| --- | --- |
| Starch | 4.00 |
| Soybean meal | 2.00 |
| Cornsteep liquor | 0.05 |
| $K_2HPO_4$ | 0.05 |
| $MgSO_4 . 7 H_2O$ | 0.05 |
| KCl | 0.03 |
| $CaCO_3$ | 0.1 |
| Water | to 100.00 |

EXAMPLE 2

Preparation of Inoculum

*Micromonospora olivoasterospora* ATCC 21819 is used as a seed strain and is initially cultured in a first seed medium containing 2% glucose, 0.5% peptone, 0.5% yeast extract and 0.1% calcium carbonate (pH 7.2 before sterilization) by inoculating one loopful of the seed strain into 10 ml of the seed medium in a 50 ml large test tube. Culturing is carried out at 30° C. for 5 days with shaking. Ten ml of the seed culture broth is then inoculated into 30 ml of a second seed medium in a 250 ml Erlenmeyer flask. The composition of the second seed medium is the same as that of the first seed medium. The second seed culturing is carried out at 30° C. for two days with shaking.

Then 30 ml of the second seed culture broth is inoculated into 300 ml of a third seed medium in a two liter Erlenmeyer flask provided with baffles. The composition of the third seed medium is the same as that of the first seed medium and the third seed culturing is carried out at 30° C. for 2 days with shaking. Thereafter, 1.5 liters of the third seed culture broth (corresponding to the contents of five flasks) is inoculated into 15 liters of a fourth seed medium in a 30 liter glass jar fermenter. The composition of the fourth seed medium is the same as that of the first seed medium. Culturing in the jar fermenter is carried out at 30° C. for two days with aeration (15 liters/min) and stirring (350 r.p.m.).

EXAMPLE 3

Production of Fortimicin AK

Fifteen liters of the fourth seed culture broth of Example 2 is inoculated into 150 liters of a main fermentation medium in a 300 liter stainless steel fermenter. The main fermentation medium comprises: 4% starch, 2% soybean meal, 1% corn steep liquor, 0.05% $K_2HPO_4$, 0.05% $MgSO_4.7H_2O$), 0.3% KCl and 0.1% $CaCO_3$ and water.(pH 7.0 before sterilization). Culturing in the fermenter is carried out at 30° C. for 4 days with aeration (80 liters/min) and stirring (150 r.p.m.).

EXAMPLE 4

Isolation of Fortimicin AK

To 5000 liters of the fermentation broth, prepared as described above, is added 102 liters of a weakly acidic carboxylic (polymethacrylate) type cation exchange resin in the ammonia form, e.g. Amberlite IRC-50 sold by the Rohm and Haas Company. The mixture is agitated for two hours, during which time the mixture is maintained at pH 6.6 by the addition of sulfuric acid. The ion exchange resin is separated from the broth by centrifugation and then added to a column and backwashed with deionized water until free of extraneous solids. The column is washed with water, then eluted downflow with 1 N ammonium hydroxide. Elutes of pH 9.6 to about 11.3 are collected and concentrated under reduced pressure until excess ammonia is removed. The solution is adjusted to pH 2.0 with hydrochloric acid and treated with 5% (w/v) activated carbon such as Pittsburgh RB carbon sold by Calgon Corporation. The solution is then filtered through a diatomaceous earth mat and the filtrate concentrated under reduced pressure to to give a mixture of crude fortimicins and metabolites.

A portion of the crude fortimicins (265 g.), prepared as described above, is dissolved in 8 liters of water and the solution adjusted to pH 9 with ammonium hydroxide. To facilitate isolation of fortimicin AK, fortimicin A is hydrolyzed to fortimicin B by heating the solution to 70° C. for 20 hours, maintaining a pH 9 by the controlled addition of ammonium hydroxide. After filtration through a mat of diatomaceous earth, the reaction mixture is concentrated under reduced pressure to approximately 3.6 liters. A portion of this material (1.8 liters) is diluted to 15 liters with water and adjusted to pH 6.8 with hydrochloric acid. The solution is charged on a column containing 7 liters of a weakly acidic, carboxylic(polymethacrylic) type, cation exchange resin in the ammonia form, e.g. Amberlite JRC-50. After washing with water, the column is eluted with 20 liters of 0.1 N ammonium hydroxide. One liter fractions are collected and examined by thin layer chromatography using Whatman No. 1 filter paper. Development is carried out at room temperature for 10 to 15 hours using a solvent system consisting of the lower phase of a mixture of methanol-chloroform-concentrated ammonium hydroxide[1:1:1(v/v/v)].

Fractions 1-2: Unidentified minor components
Fractions 3-4: Isofortimicin
Fraction 5: Isofortimicin and fortimicin B
Fractions 6-10: Fortimicin B Fractions 11–20: Unidentified minor components Crude isofortimicin (38 g) (fractions 3-4) is chromatographed on a column (105 cm×4 cm diameter) of Woelm silica gel (0.032–0.063 mm diameter) developed with the lower phase of a mixture of chloroform, methanol and concentrated ammonium hydroxide [2:1:1(v/v/v)]. Initial column fractions contained isofortimicin. Subsequent fractions are pooled and concentrated to give 2.2 g of crude fortimicin AK. The crude product is purified by chromatography on a column (27 cm×2 cm diameter) of Woelm silica gel developed with the lower phase of a mixture of chloroform-isopropanol-concentrated ammonium hydroxide[4:2:1 (v/v/v)]. Later fractions are combined and concentrated to yield fortimicin AK (647 mg). Proton magnetic resonance spectrum in deuterium oxide with tetramethylsilane as an external reference: $\delta 2.90(3H)$ singlet $NCH_3$; $\delta 4.05(3H)$ singlet $OCH_3$; $\delta 5.57 (1H)$ doublet $C_{1'}$-H.

The invention claimed is:

1. Fortimicin AK represented by the formula

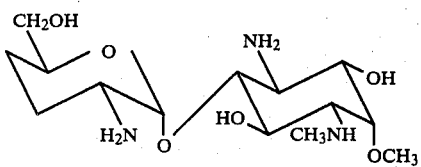

or a pharmaceutically acceptable salt thereof.

* * * * *